(12) United States Patent
Park

(10) Patent No.: US 9,040,557 B2
(45) Date of Patent: May 26, 2015

(54) COMPOSITION CONTAINING CINCHONINE AS AN ACTIVE INGREDIENT FOR PREVENTING AND TREATING OBESITY, DYSLIPIDEMIA, FATTY LIVER, OR INSULIN RESISTANCE SYNDROME

(75) Inventor: Tae Sun Park, Seoul (KR)

(73) Assignee: YONSEI UNIVERSITY TECHNOLOGY HOLDINGS, INC., Incheon (KR)

( * ) Notice: Subject to any disclaimer, the term of this patent is extended or adjusted under 35 U.S.C. 154(b) by 5 days.

(21) Appl. No.: 13/578,717

(22) PCT Filed: Dec. 14, 2010

(86) PCT No.: PCT/KR2010/008944
§ 371 (c)(1),
(2), (4) Date: Sep. 5, 2012

(87) PCT Pub. No.: WO2011/090265
PCT Pub. Date: Jul. 28, 2011

(65) Prior Publication Data
US 2012/0322822 A1    Dec. 20, 2012

(30) Foreign Application Priority Data
Jan. 19, 2010 (KR) .......................... 10-2010-0004901

(51) Int. Cl.
*A61K 31/4409* (2006.01)
*A61K 31/47* (2006.01)
*A61K 31/4709* (2006.01)
*A61K 31/49* (2006.01)
*A61K 31/439* (2006.01)

(52) U.S. Cl.
CPC ............. *A61K 31/4409* (2013.01); *A61K 31/47* (2013.01); *A61K 31/4709* (2013.01); *A61K 31/49* (2013.01); *A61K 31/439* (2013.01)

(58) Field of Classification Search
CPC ... A61K 31/4409; A61K 31/47; A61K 31/49; A61K 31/439
See application file for complete search history.

(56) References Cited

U.S. PATENT DOCUMENTS

2004/0028759 A1    2/2004   Maurel et al.
2006/0052351 A1    3/2006   Platt et al.

OTHER PUBLICATIONS

Al-Mustafa et al. 2008. Pakistan Journal of Biological Sciences, vol. 11 (3), pp. 351-358.*
Chung et al. 1987, Planta medica, vol. 53 (2), pp. 206-210.*
Shah et al. 1998, Biochemical Pharmacology, vol. 56, pp. 955-960.*
Lacoste et al. 1995, Circulation, vol. 92, pp. 3172-3177.*
International Search Report from PCT/KR2010/008944 dated Aug. 25, 2012 (date of completion of search) and Aug. 29, 2011 (date of mailing of search report).

* cited by examiner

*Primary Examiner* — Kara R McMillian
(74) *Attorney, Agent, or Firm* — Clark & Elbing LLP

(57) ABSTRACT

The present invention relates to a composition for preventing or treating obesity, dyslipidemia, fatty liver or insulin resistance syndrome, comprising cinchonine as an active ingredient. The composition of the present invention comprising cinchonine as an active ingredient contributes to not only inhibition of adipocyte differentiation but also reductions of body weight, visceral fat, total cholesterol level, plasma triglyceride level and liver tissue triglyceride level, thereby exerting prevention or treatment efficacies of obesity, hyperlipidemia or fatty liver. In addition, the composition of the present invention induces significant decrease in fasting glucose level and blood insulin level to improve type 2 diabetes, insulin resistance and related metabolic diseases.

13 Claims, 6 Drawing Sheets

COMPOSITION CONTAINING CINCHONINE AS AN ACTIVE INGREDIENT FOR PREVENTING AND TREATING OBESITY, DYSLIPIDEMIA, FATTY LIVER, OR INSULIN RESISTANCE SYNDROME

CROSS-REFERENCE TO RELATED APPLICATIONS

This application is the U.S. national stage filing under 35 U.S.C. §371 of international application PCT/KR2010/008944, filed Dec. 14, 2010, which claims benefit of Korean Patent Application No. 10-2010-0004901, filed Jan. 19, 2010.

FIELD OF THE INVENTION

The present invention relates to a composition for preventing or treating obesity, dyslipidemia, fatty liver or insulin resistance syndrome, comprising cinchonine as an active ingredient.

DESCRIPTION OF THE RELATED ART

Changes in life styles and living environments result in a pathogenic increase of visceral adiposity in modern people. Frequent occurrence of visceral obesity in turn leads to a rapid increase in development of metabolic syndromes which are accompanied by diabetes, hypertension, lipid metabolism disorders, insulin resistance and the like. These attendant diseases increase a mutual risk factor and are common diseases which are associated with a variety of metabolic changes such as senescence, stress conditions, compromised immune function and the like.

Obesity induces chronic disease such as fatty liver, hypertension, diabetes and cardiovascular diseases as well as ugly appearance. 31.7% of Korean adults show obesity according to the 2007 National Health and Nutrition Survey of the Korean Ministry of Health and Welfare, addressing that three of ten adult persons are susceptible to complications of obesity. The increase in overweight and obese population is in turn responsible for elevated increased risk of chronic diseases. The number of diabetic patients in Korea is 3,000,000 in 2007 and estimated to be 5,450,000 in 2030 that corresponds to 10% of Korean population. The mortality rate of diabetes in Korea is 35.5 persons per 100,000 persons, which is higher 3-7 folds than that in Japan (5.9 persons), England (7.5 persons) and Germany (16.6 persons).

According to statistics of Korea Institute for Health and Social Affairs, the socioeconomic loss caused by obesity and obesity-related complications in 2006 is estimated at 2.1 trillion won including medical cost and indirect cost such as loss of earning. Thus, in 2010, the Korean government has decided to reduce the obesity rate down to 20% in adults and to 15% in youth. To strategies for achieving the aims, the government has been looking for the exact definition and measuring method about obesity and metabolic diseases.

At present, 1.7 billion people amounting to about 25% of the world population are overweight (BMI>25) and more than 300 million people including 120 million in the US, Europe and Japan are classified as obese (BMI>30). Among the OECD countries, the US has the highest obesity rate of 31% of population, followed by Mexico (24%), England (23%), Greece (22%), Australia (22%), New Zealand (21%), Hungary (19%), Canada (14%), Spain (13%), Ireland (13%), Germany (13%), Portugal (13%), Finland (13%), Turkey (12%) and Belgium (12%). The number of obese people in China is 70 million and the body weight control-related market is expanding, estimated at about 10 billion yuan. Childhood obesity is also increasing rapidly worldwide, with 1 in 5 children being obese. As such, childhood obesity is becoming a serious social issue. Since childhood obesity is the main cause of the life style diseases including diabetes, hypertension, stroke, etc. with increased blood cholesterol and triglyceride level, 80% or more of obese children are likely to become obese adults. Further, since increased fat stimulates secretion of sex hormones and induces early adolescence, childhood obesity may cause growth problems. Also, it negatively affects blood circulation and nourishment.

Obesity drugs that are marketed inside and outside Korea include 'Xenical' (Roche Korea) with orlistat as main ingredient and approved by the FDA, 'Reductil' (Ilsung Pharmaceuticals) with sibutramine as main ingredient, 'Exolise' (Guju Pharma) with green tea catechol as main ingredient, or the like. Xenical, which reduces absorption of fat by inhibiting lipase, has the gastrointestinal-related side effects such as steatorrhea, gas generation and reduced absorption of oil-soluble vitamins. Reductil, which increases serotonin and noradrenaline levels in the sympathetic nervous system, has side effects such as headache, dry mouth, loss of appetite, insomnia, constipation, etc. Besides, a large number of anti-obesity drugs have been withdrawn from the market due to severe side effects. For example, aminophylline is reported to have various side effects in the nervous, circulatory and digestive systems despite its excellent effect of reducing body fat. Also, fenfluramine, dexfenfluramine, topiramate, ephedrine, etc. have been banned from being marketed as obesity drugs. As the synthetic drugs show limitations in side effects and in overcoming chronic diseases, foods and drugs derived from natural sources are drawing attentions.

Throughout the specification, a number of publications and patent documents are referred to and cited. The disclosure of the cited publications and patent documents is incorporated herein by reference in its entirety to more clearly describe the state of the related art and the present disclosure.

DETAILED DESCRIPTION OF THIS INVENTION

Technical Purposes of this Invention

The present inventor has made intensive studies to develop novel natural substance or compounds derived from natural sources having therapeutic efficacies for metabolic diseases including obesity, dyslipidemia and/or fatty liver. As a result, the present inventor has found that cinchonine obtainable from various plants is significantly effective in prevention or treatment of the metabolic diseases.

Accordingly, it is an object of this invention to provide a composition for preventing or treating obesity, dyslipidemia, fatty liver or insulin resistance syndrome.

It is another object of this invention to provide a method for preventing or treating obesity, dyslipidemia, fatty liver or insulin resistance syndrome.

Other features and aspects will be apparent from the following detailed description, drawings and claims.

Technical Solutions of this Invention

In one aspect of the present invention, there is provided a composition for preventing or treating metabolic diseases, comprising: cinchonine as an active ingredient; wherein the metabolic disease is obesity, dyslipidemia, fatty liver or insulin resistance syndrome.

In another aspect of the present invention, there is provided a method for preventing or treating metabolic diseases, comprising: administering the composition comprising cinchonine as an active ingredient to a subject in need thereof; wherein the metabolic disease is obesity, dyslipidemia, fatty liver or insulin resistance syndrome.

The present inventor has made intensive studies to develop novel natural substance or compounds derived from natural sources having therapeutic efficacies for metabolic diseases including obesity, dyslipidemia and/or fatty liver. As a result, I have found that cinchonine obtainable from various plants is significantly effective in prevention or treatment of the metabolic diseases.

As demonstrated in Examples, cinchonine contributes to inhibition of adipocyte differentiation but also reductions of body weight, visceral fat, total cholesterol level, plasma triglyceride level and liver tissue triglyceride level, thereby considerably ameliorating obesity induced by high fat diets. In addition, cinchonine induces significant decrease in fasting glucose level, which leads to improved type 2 diabetes, insulin resistance and related metabolic diseases.

The term used herein "dyslipidemia" refers to hyperlipidemia, including abnormal lipid conditions caused by aberrant lipoprotein metabolism as well as hypercholesterolemia, hypertriglyceridemia and low HDL-cholesterolemia.

The term "hyperlipidemia" refers to a disease caused by higher level of blood lipids due to abnormal metabolism of lipids such as triglyceride and cholesterol. More specifically, hyperlipidemia is characterized by increased levels of lipids such as triglyceride, LDL cholesterol, phospholipids and free fatty acids in blood, including hypercholesterolemia and hypertriglyceridemia.

As used herein, the term "fatty liver" refers to a condition where fat accumulates excessively in liver cells due to the disorder of lipid metabolism. It may cause various diseases such as angina, myocardial infarction, stroke, arteriosclerosis and pancreatitis.

As used herein, the term "diabetes" refers to a chronic disease characterized by relative or absolute lack of insulin, leading to glucose intolerance. As used herein, the term diabetes includes all kinds of diabetes, such as type 1 diabetes, type 2 diabetes and genetic diabetes. Type 1 diabetes, which is insulin-dependent diabetes, mainly results from the destruction of β-cells. Type 2 diabetes, which is non-insulin-dependent diabetes, is caused by insufficient secretion of insulin after meals or by insulin resistance.

As used herein, the term "insulin resistance" refers to a condition in which the natural hormone insulin becomes less effective at lowering blood sugars. When insulin resistance becomes apparent, the human body creates too much insulin to result in developments of not only hypertension and dyslipidemia but also heart diseases and diabetes. Especially, in type 2 diabetes, the increase in insulin is unrecognized in muscle and fat tissue, such that insulin action does not occur.

As used herein the term "insulin resistance syndrome" refers to a general term for disease which is induced by insulin resistance. It is characterized by cell resistance against insulin action, hyperinsulinemia, increase of very low density lipoprotein (VLDL) and triglyceride, decrease of high density lipoprotein (HDL) and hypertension. The insulin resistance syndrome is usually considered as a risk factor for cardiovascular disease and type 2 diabetes (Reaven G M, Diabetes, 37:1595-607 (1988)). In addition, it has been reported that insulin resistance increases intracellular oxidative stress together with risk factors such as hypertension, diabetes and smoking, and alters signal transduction to cause inflammatory responses, such that atherosclerosis is developed (Freeman B A. Et al., Lab Invest. 47: 412-26, (1982)), Kawamura M. et al, J Clin Invest. 94: 771-8 (1994)).

As used herein the term "metabolic diseases" refer to a group of a wide variety of diseases caused by risk factors for various cardiovascular diseases and type 2 diabetes, including insulin resistance and its related diverse and complicated metabolic and clinical abnormalities. In 1988, Reaven suggested that a common cause of these symptoms is insulin resistance and named insulin resistance syndrome; however, in 1998, WHO newly introduced the term "metabolic syndrome or metabolic diseases", because insulin resistance may not explain all the elements of these symptoms.

Cinchonine used as active ingredients is one of alkaloid compounds contained various plants including *Cinchona, Cinchona officinalis, Cinchona pubescens, Olea europaea* and *Smilax china*. Its chemical formula is $C_{19}H_{22}N_2O$ and molecular weight is 294.4. Cinchonine is represented by the following formula:

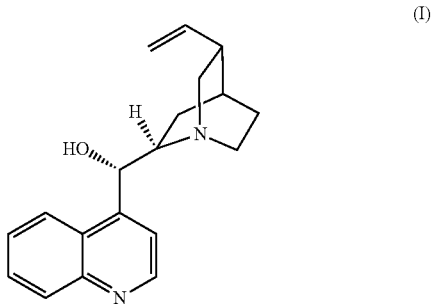 [SMILES: C=CC1CN2CCC1C[C@@H]2[C@@H](O)c1ccnc2ccccc12]

(I)

Cinchonine was reported to improve multi-drug resistance of cancer cells through P-glycoprotein binding [Reference: Ruiz-Mesia L, Ruiz-Mesía W, Reina M, Martínez-Diaz R, de Inés C, Guadaño A, González-Coloma A. Bioactive cinchona alkaloids from Remijia peruviana. J Agric Food Chem. 2005 Mar. 23; 53(6):1921-6]. Furthermore, cinchonine was suggested to induce apoptosis by suppressing transportation of drugs from P388 multidrug-resistant cells [Reference: Furusawa S, Nakano S, Wu J, Sakaguchi S, Takayanagi M, Sasaki K I, Satoh S. Apoptosis induced by doxorubicin and cinchonine in P388 multidrug-resistant cells. J Pharm Pharmacol. 2001 Jul.; 53(7):1029-39]. Cinchonine was also reported to exhibit in vitro anti-malaria effects [Reference: Druilhe P, Brandicourt O, Chongsuphajaisiddhi T, Berthe J. Activity of a combination of three cinchona bark alkaloids against *Plasmodium falciparum* in vitro. Antimicrob Agents Chemother. 1988 February; 32(2):250-4]. In addition to this, cinchonine inhibits platelet aggregation by blocking $Ca^{2+}$ influx into human platelets [Reference: Shah B H, Nawaz Z, Virani S S, Ali I Q, Saeed S A, Gilani A H. The inhibitory effect of cinchonine on human platelet aggregation due to blockade of calcium influx. Biochem Pharmacol. 1998 Oct. 15; 56(8): 955-60], and shows antihypertensive effects by blocking adrenorceptor and $Ca^{2+}$ channels [Reference: Gilani A H, Shaheen F. Studies on dual antihypertensive activity of cinchonine: an alkaloid from cinchona bark. In: Symposium on Bioassay Methods in Natural Product Research and Drug Development. 1997].

The present composition comprising cinchonine as active ingredients has efficacies to improve various metabolic diseases such as obesity, dyslipidemia, fatty liver or insulin resistance syndrome. The present composition exhibits therapeutic efficacies on metabolic diseases by various physiological activities.

According to a preferred embodiment, the present composition reduces differentiation of adipocytes to show prevention or treatment efficacies on obesity. As addressed in Examples, the present composition decreases differentiation of adipocyte precursor cells in a dose-dependent manner to show prevention or treatment efficacies on obesity (see FIGS. 1a-1b).

The term "liver" or "visceral" is used to encompass organ, tissue and cell.

The term used herein "level" refers to the amount of certain component contained in a sample (e.g., blood and tissue), and interchangeably with the term "amount".

According to a preferred embodiment, the present composition significantly decreases blood fat, more preferably triglyceride, cholesterol or free fatty acids in blood, thereby exhibiting prevention or treatment efficacies on dyslipidemia, especially hyperlipidemia. As demonstrated in Examples, the group fed with the present composition showed significantly lower plasma levels of triglyceride (by 24%), total cholesterol (by 30%), HDL cholesterol (by 25%), LDL+VLDL cholesterol (by 33%) and free fatty acid (by 21%) as compared to the high fat diet group, thereby exhibiting excellent prevention or treatment efficacies on dyslipidemia caused by metabolic diseases, especially hyperlipidemia (see Table 2).

According to a preferred embodiment, the present composition significantly decreases liver fat, more preferably triglyceride, cholesterol or free fatty acids in liver, thereby exhibiting prevention or treatment efficacies on fatty liver. In Examples, the present composition was analyzed to significantly decrease triglyceride, cholesterol or free fatty acid levels in liver (see Table 3).

According to a preferred embodiment, the present composition reduces visceral fat, more preferably epididymal fat, perirenal fat, mesenteric fat or retroperitoneal fat, so that it can prevent or treat obesity. In Examples, the present composition was elucidated to significantly decrease weights of total visceral fat, epididymal fat, perirenal fat, mesenteric fat and retroperitoneal fat, exhibiting efficacies to prevent or treat obesity (see FIG. 3).

"ALT (alanine aminotransferase)" and "AST (aspartate aminotransferase)" as indicators for liver function are enzymes exhibiting increased levels in blood upon damage of liver.

According to a preferred embodiment, the composition of the present invention considerably decreases levels of ALT or AST in blood. In Examples, the present composition was investigated that the group fed with the present composition showed significantly decreased plasma levels of ALT (by 58%) and AST (by 46%) as compared to the high fat diet group, demonstrating that the present composition can ameliorate fatty liver, more preferably non-alcoholic fatty liver conditions to improve fatty liver (see Table 2).

The aP2 (fatty acid binding protein) gene is expressed in proliferation and differentiation of preadipocytes to adipocytes, under controls of PPARγ (Peroxisome proliferator activated receptor gamma) and C/EBPs (CCAAT enhancer-binding proterins).

According to a preferred embodiment, the composition of the present invention decreases the expression of PPARγ, C/EBPs or aP2. The present composition decreases the expressions of PPARγ and C/EBPs, and in turn their target gene aP2, showing effects on reducing the amount of visceral fat (see FIG. 3).

It has been reported that when obesity is induced by HFD, free fatty acids (especially saturated fat) in body fluids are increased. The free fatty acids as ligands bound to TLR4 activate IKK and then NF-κB, and stimulate the secretion of pro-inflammatory cytokines such as TNF-α and IL-6 to cause inflammatory response. In addition, TNF-α and IL-6 activate both the cytokine signaling 3 (SOCS3) and JNK and induce phosphorylation of serine residues of insulin receptor substrates (IRS) to inhibit glucose transport, finally causing insulin resistance in peripheral tissues of liver or muscle.

According to a preferred embodiment, the composition of the present invention may prevent or treat insulin resistance syndromes, more preferably, obesity, hypertension, atherosclerosis, hyperlipidemia, hyperinsulinemia, non-alcoholic fatty liver or type 2 diabetes caused by insulin resistance. In accordance with one example of the present invention, the present composition decreases the expression of TNF-α and IL-6 (see FIG. 5), addressing that cinchonine contained in the present composition prevents or treats chronic inflammation and insulin resistance of visceral fat tissues caused by obesity.

"UCP2 (uncoupling protein 2)" and "UCP3 (uncoupling protein 3)" are mitochondrial proteins and found mainly in adult adipocytes and skeletal muscles, respectively. These proteins lead to heat generation in mitochondria to increase cellular energy consumption, which act as excellent targets for anti-obesity drugs.

According to a preferred embodiment, the composition of the present invention increases the expression of UCP2 (uncoupling protein 2) or UCP3 (uncoupling protein 3). Cinchonine as active ingredients increases expressions of mitochondrial thermogenesis proteins, UCP2 and UCP3 in cells to promote thermogenesis, finally exhibiting anti-obesity effects.

According to an embodiment, the composition of the present invention decreases glucose or insulin level in plasma. As demonstrated in Examples, the composition of the present invention significantly reduced fasting blood sugar level (by 27%) to improve insulin resistance, thereby exhibiting therapeutic efficacies for metabolic diseases.

According to an embodiment, cinchonine contained in plant extracts or fractions may be used.

Cinchonine may be extracted or fractionated from plants, preferably *Cinchona antioquiae, Cinchona asperifolia, Cinchona barbacoensis, Cinchona×boliviana, Cinchona calisaya, Cinchona capuli, Cinchona fruticosa, Cinchona glandulifera, Cinchona hirsuta, Cinchona krauseana, Cinchona lancifolia, Cinchona ledgeriana, Cinchona lucumifolia, Cinchona macrocalyx, Cinchona micrantha, Cinchona mutisk Cinchona nitida, Cinchona officinalis, Cinchona parabolica, Cinchona pitayensis, Cinchona pubescens, Cinchona pyrifolia, Cinchona rugosa, Cinchona scrobiculata, Cinchona villosa, Cinchona succirubra, Cinchona robusta, Cinchona hybrida, Olea europaea,* or *Smilax china.*

The plant extracts containing cinchonine may be prepared using various extraction solvents. Preferably, the extraction solvent includes (a) absolute or hydrous lower alcohol containing 1-4 carbon atoms (e.g., methanol, ethanol, propanol, butanol, n-propanol, iso-propanol and n-butanol), (b) mixture of lower alcohol and water, (c) acetone, (d) ethyl acetate, (e) chloroform, (f) 1,3-butyleneglycol, (g) hexane, (h) diethylether, (i) butyl acetate or (j) water.

The plant fractions containing cinchonine may be obtained by additional isolation/purification of the plant extracts to give further isolated/purified forms. For instance, it could be appreciated that active fractions obtained using a variety of additional purification methods such as an ultrafiltration with defined molecular weight cut-off value and various chromatography (designed for purification dependent upon size, charge, hydrophobicity and affinity) are included in the present plant fractions.

Alternatively, cinchonine may be chemically synthesized.

According to a preferred embodiment, cinchonine may be an isolated form from plants or chemical-synthesized form.

In still another aspect of this invention, there is provided a pharmaceutical composition or a food composition for preventing or treating a metabolic disease, comprising: cinchonine as an active ingredient; wherein the metabolic disease is obesity, dyslipidemia, fatty liver or insulin resistance syndrome.

When the composition of the present disclosure is prepared as a pharmaceutical composition, the pharmaceutical composition of the present disclosure may comprise a pharmaceutically acceptable carrier. The pharmaceutically acceptable carrier included in the pharmaceutical composition of the present disclosure is one commonly used in the preparation of formulations and includes lactose, dextrose, sucrose, sorbitol, mannitol, starch, gum acacia, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present disclosure may further include, in addition to the above-described components, a lubricant, a wetting agent, a sweetener, a fragrance, an emulsifier, a suspending agent, a preservative, or the like. Suitable pharmaceutically acceptable excipients and formulations are described in detail in *Remington's Pharmaceutical Sciences* (19$^{th}$ ed., 1995).

The pharmaceutical composition of the present disclosure may be administered orally or parenterally. Preferably, it may be administered parenterally.

An appropriate administration dosage of the pharmaceutical composition of the present disclosure may be determined variously depending on such factors as preparation method, administration method, age, body weight and gender of a patient, pathological condition, diet, administration time, administration route, excretion rate or response sensitivity. Specifically, a daily dosage of the pharmaceutical composition of the present disclosure may be 0.001-100 mg/kg.

The pharmaceutical composition of the present disclosure may be prepared into a unit dosage form or multiple dosage form along with a pharmaceutically acceptable carrier and/or excipient according to a method that can be easily employed by those skilled in the art. The formulation may be in the form of solution in oily or aqueous medium, suspension, syrup, emulsion, extract, dust, powder, granule, tablet or capsule, and may further include a dispersant or stabilizer.

When the composition of the present disclosure is prepared as a food composition, the food composition of the present disclosure may comprise, in addition to cinchonine as the active ingredient, ingredients commonly added for preparation of food. For example, proteins, carbohydrates, fats, nutrients, seasoning or flavors may be added. The carbohydrate may be, for example, a sugar such as a monosaccharide, e.g. glucose, fructose, etc., a disaccharide, e.g. maltose, sucrose, oligosaccharide, etc. or a polysaccharide, e.g. dextrin, cyclodextrin, etc. or a sugar alcohol such as xylitol, sorbitol, erythritol, etc. The flavor may be a natural flavor [thaumatin, stevia extract (e.g. rebaudioside A, glycyrrhizin, etc.]) or a synthetic flavor (saccharin, aspartame, etc.).

For example, when the food composition of the present disclosure is prepared as a drink, it may further comprise, in addition to cinchonine of the present disclosure as the active ingredient, citric acid, high-fructose corn syrup, sugar, glucose, acetic acid, malic acid, fruit juice, eucommia extract, jujube extract, licorice extract, or the like.

Advantageous Effects of this Invention

The features and advantages of the present invention may be summarized as follows:
(i) The present invention provides a composition for preventing or treating obesity, dyslipidemia, fatty liver or insulin resistance syndrome, comprising cinchonine as an active ingredient.

(ii) The active ingredient may be isolated from various plants and chemically synthesized.

(iii) The composition of the present invention comprising cinchonine as an active ingredient contributes to not only inhibition of adipocyte differentiation but also reductions of body weight, visceral fat, total cholesterol level, plasma triglyceride level and liver triglyceride level, thereby exerting prevention or treatment efficacies of obesity, hyperlipidemia or fatty liver. In addition, the composition of the present invention induces significant decrease in fasting glucose level and blood insulin level to improve type 2 diabetes, insulin resistance and related metabolic diseases.

BRIEF DESCRIPTION OF THE DRAWINGS

FIG. 1a shows results from 3T3L1 cells incubated with (+)-cinchonine, addressing that cinchonine significantly decreases differentiation of adipocyte precursor cell in a dose-dependent manner. FIG. 1b shows relative quantitative analysis results by a spectrophotometer for the content of intracellular fat stained by Oil-red O. The O.D. values were measured to be decreased in a dose-dependent manner. HFD corresponds to high fat diet, CISD to cinchonine-supplemented high fat diet and ND to normal diet.

PREFERRED EXAMPLES OF THIS INVENTION

The present invention will now be described in further detail by examples. It would be obvious to those skilled in the art that these examples are intended to be more concretely illustrative and the scope of the present invention as set forth in the appended claims is not limited to or by the examples.

EXAMPLES

As used herein and unless otherwise indicated, the solid/solid is expressed by (weight/weight) part or %, the solid/liquid by (weight/volume) part or %, and the liquid/liquid by (volume/volume) part or %.

Example 1

Inhibitory Effects of Cinchonine on Apipocyte Differentiation Using Mouse Adipocyte Cell Line (3T3-L1)

Cell Culture and Oil-Red O Staining

The effects of cinchonine (Sigma-Aldrich) on adipocyte differentiation and proliferation were investigated using mouse adipocyte cell line (3T3-L1, ATCC, USA). 3T3-L1 cells as adipocyte precursor cells were plated on a 12-well plate containing DMEM supplemented with 1% penicillin-streptomycin (Hyclone, USA), 1% non-essential amino acids (Hyclone, USA) and 10% fatal bovine serum (Hyclone, USA) and cultured to a confluent state in a 37° C., 5% $CO_2$ incubator. The 3T3-L1 cells were then cultured for two days in a medium containing DMI [0.5 mM isobutyl-methylxanthine (Sigma-Aldrich), 1 μM dexamethason (Sigma-Aldrich) and 1 μg/mL insulin (Sigma-Aldrich)] to be differentiated into adipocytes, and further cultured for two days in DMEM containing 1 μg/mL insulin to be differentiated into mature adipocytes. Afterwards, cells were cultured for ten days with changing DMEM every other day to form fully differentiated adipocytes.

Figure 1A:
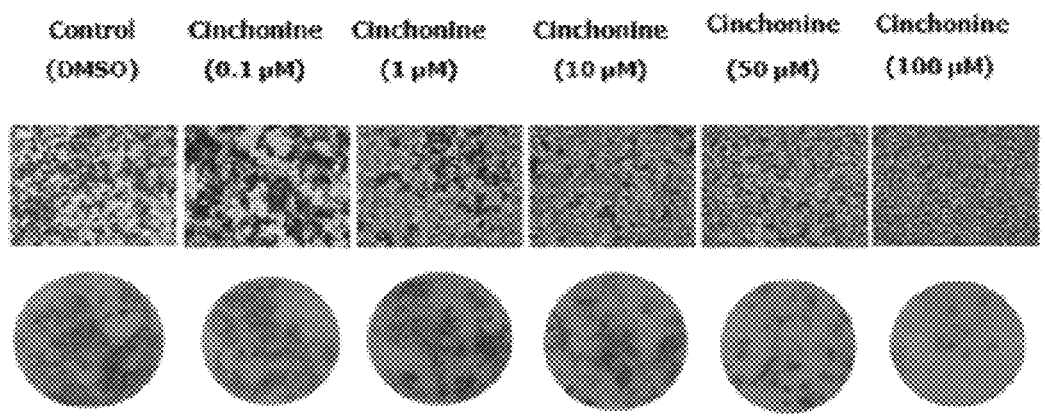
FIGS. 1a-1b represent inhibition of adpipocyte differentiation in 3T3L1 cells by cinchonine.
Figure 1B:
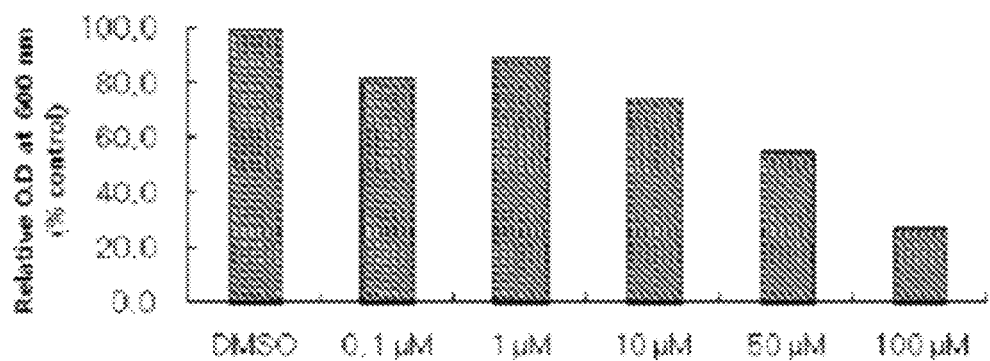

From the first day of the adipocyte differentiation in a medium containing DMI, 3T3-L1 cells were treated with 0.1, 1, 10, 50 and 100 μM (+)-cinchonine. (+)-Cinchonine was purchased from Sigma-Aldrich, Inc. and dissolved in DMSO for use. The negative control containing only DMSO was prepared. Following the fourteen-day culture exhibiting a full differentiation, the medium was discarded and fat globules contained in adipocytes were stained. For the staining, cells were washed twice with PBS (phosphate buffered saline) and fixed for 1 hr using 10% BNF (buffered neutral formalin), followed by additionally washing once with PBS. Then, 1 mL of oil-red O dye, which stains fat globules specifically in red color, was added to the 12-well plate to stain fat globules for 1 hr, followed by repeated washing with distilled water. To measure concentrations of triglyceride in the differentiated 3T3-L1 cells, the stained fat globules were dissolved in isobutanol and the O.D. values at 600 nm were measured.
Inhibitory Effects of Cinchonine on Adipocyte Differentiation As shown in FIG. 1a, (+)-cinchonine decreased differentiation of 3T3-L1 adipocyte precursor cells in a dose-dependent manner. The content of intracellular fats stained with Oil-red O was decreased by (+)-cinchonine in a dose-dependent manner as measured with a spectrophotometer (Versamax, MDS Analytical Technology, USA) (FIG. 1b).

Example 2

Reduction of Body and Visceral Fat-Pad Weights by Cinchonine

Preparation of Test Diets and Maintenance of Test Animals

The obesity-inducing control diet used in the test was high-fat diet (HFD: 40% fat calorie, 17 g lard+3% corn oil/100 g diet). Diets supplemented with cinchonine (cinchonine-supplemented high fat diet, CSID) had the same composition as HFD, except that cinchonine was included in a concentration of 0.05%. The normal diet (ND) was prepared according to the AIN-76 rodent diet composition (American Institute of Nutrition, Report of the American Institute of Nutrition ad hoc committee on standards for nutritional studies. *J. Nutr.*, 107: 1340-1348, (1977)) (FIG. 1). (+)-Cinchonine was purchased from Sigma-Aldrich.

TABLE 1

| Ingredients | Normal diet (ND) (g/kg diet) | High-fat diet (HFD) (g/kg diet) | Cinchonine-supplemented diet (CSID) (g/kg diet) |
|---|---|---|---|
| Casein | 200 | 200 | 200 |
| D/L-Methionine | 3 | 3 | 3 |
| Corn starch | 150 | 111 | 109 |
| Sucrose | 500 | 370 | 370 |
| Cellulose | 50 | 50 | 50 |
| Corn oil | 50 | 30 | 30 |
| Lard | — | 170 | 170 |
| Vitamin complex[1] | 10 | 12 | 12 |
| Mineral complex[2] | 35 | 42 | 42 |
| Choline bitartrate | 2 | 2 | 2 |
| Cholesterol | — | 10 | 10 |
| Tert-butylhydroquinone | 0.01 | 0.04 | 0.04 |
| Cinchonine | — | — | 0.5 |
| Total (g) | 1,000 | 1,000 | 1000 |
| Fat (% calorie) | 11.5 | 39.0 | 39.0 |
| Total calorie (kJ/kg diet) | 16,439 | 19,315 | 19,315 |

[1]Mineral complex (g/kg of mix): $CaHPO_4$ 500; NaCl 74; $K_2H_6O_7H_2O$ 220; $K_2SO_4$ 52; MgO 24; $MnCO_3$ 3.5; $Fe(C_6H_5O_7)\cdot 6H_2O$ 6; $ZnCO_3$ 1.6; $CuCO_3$ 0.3; $KIO_3$ 0.01; $Na_2SeO_3\cdot 5H_2O$ 0.01; $CrK(SO_4)_2$ 0.55; sugar powder 118.03.
[2]Vitamin complex (g/kg of mix): Thiamine•HCl 0.6; Riboflavine 0.6; Pyridoxine•HCl 0.7; nicotinic acid 3; D-calcium pantothenate 1.6; folic acid 0.2; D-biotin 0.02; cyanocobalamin (Vitamin B12)(0.1%) 1.0; Vitamin A palmitic acid (500,000 IU/g); Cholecalciferol (Vitamin D3)(400,000 IU/gm) 0.25; Vitamin E acetate (500 IU/g) 10; Menadione sodium bisulfite 0.08; Sugar powder 981.15.

5-week-old male C57BL/6J mice (Orient, Korea) were accustomed to the laboratory environment for 1 week while feeding solid feed. Then, they were randomly divided into a high-fat diet group and a test group according to randomized block design and bred for a total of 10 weeks. The diet was given between 10 and 11 A.M. every day together with water. Food intake was measured every day and body weight was measured once a week. In order to avoid transient body weight increase after feed intake, body weight was measured 2 hr after removing the feed. After fasting the test animal for at least 12 hr and anesthetizing with diethyl ether, blood, liver and visceral fat (epididymal fat, perirenal fat, mesenteric fat and retroperitoneal fat) were taken and weighed after washing with 0.1 M PBS (pH 7.4). Blood taken from the abdominal aorta was centrifuged at 1000×g for 15 minutes for the separation of plasma.

Changes of Body and Visceral Fat-Pad Weights

Figure 2A:
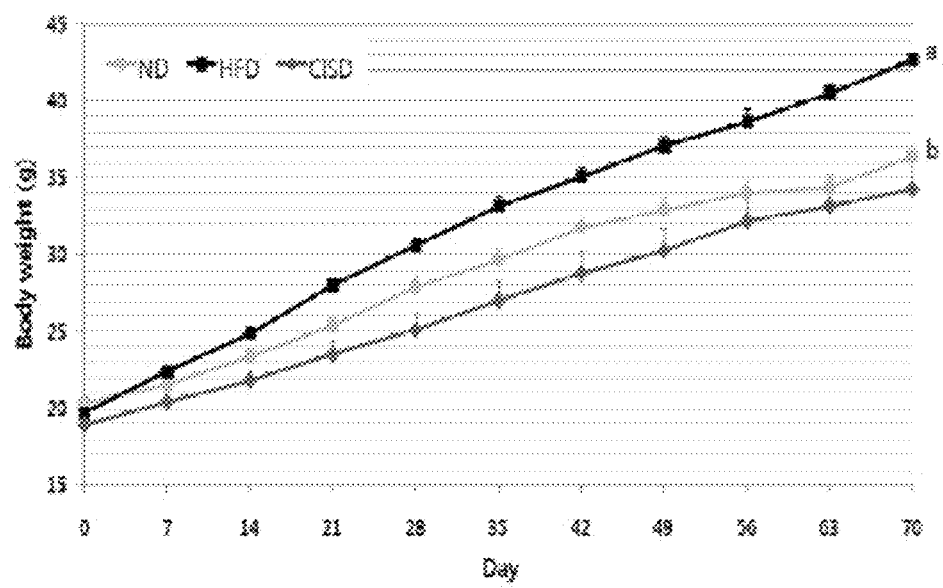
FIGS. 2a-2b represent changes of body weight and body weight gain in mice. As a result, the cinchonine-supplemented group (CSID) showed decrease in the final body weight by 20% and the cumulative body weight gain by 39% as compared to HFD. The results are represented as mean±standard error of values obtained from eight mice. The characters above the bars indicate significant difference among dietary groups by one-way analysis of variance (ANOVA) test and Duncan's multiple range test (P<0.05).
Figure 2B:
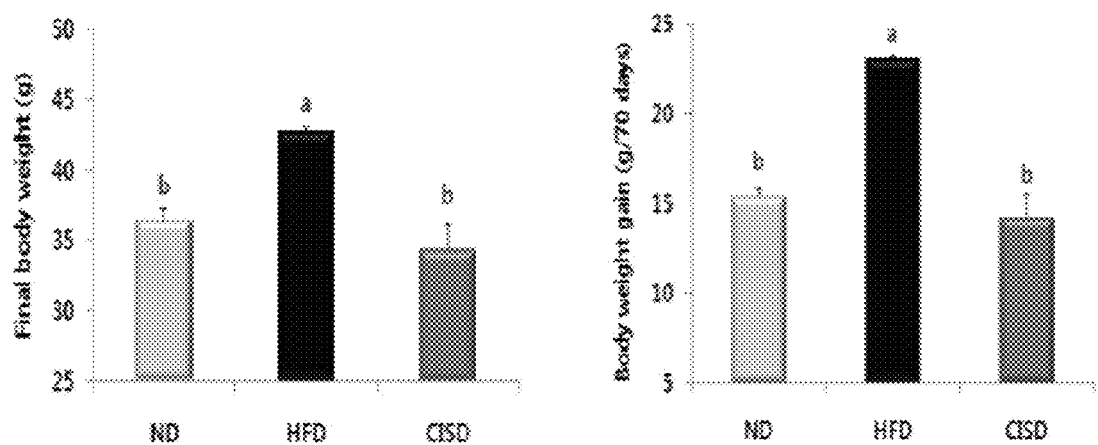

After feeding the test diet for 10 weeks, the cinchonine-supplemented group (CSID) showed decrease in the final body weight by 20% and the cumulative body weight gain by 39% as compared to HFD (FIGS. 2a-2b).

Figure 3:
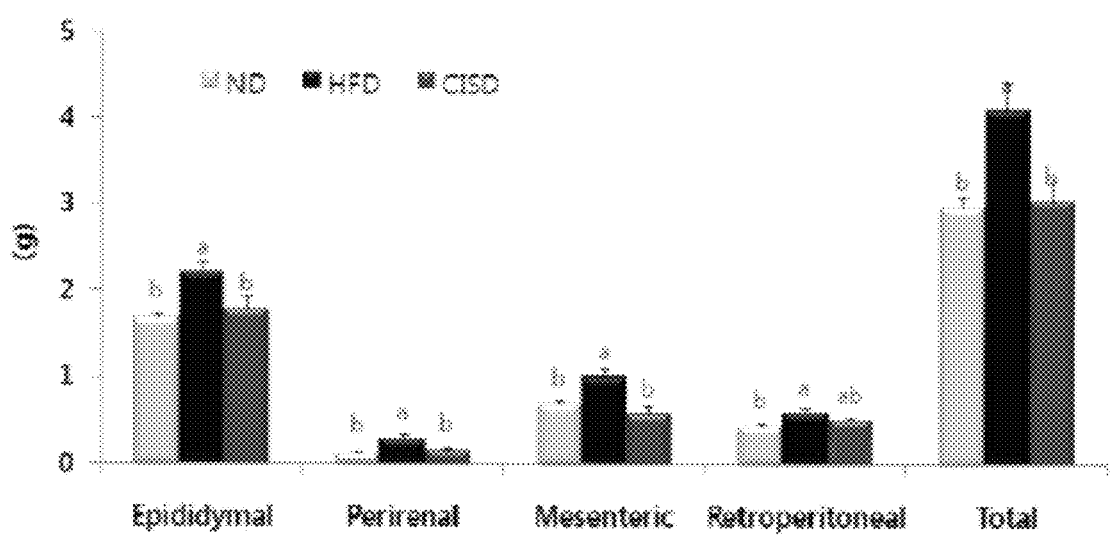
FIG. 3 represents visceral fat-pad weight of mice fed with test diets. The results are represented as mean±standard error of values obtained from eight mice. The characters above the bars indicate significant difference among dietary groups by one-way analysis of variance (ANOVA) test and Duncan's multiple range test (P<0.05). Epididymal refers to weight of epididymal fat, Perirenal to weight of perirenal fat, Mesenteric to weight of mesenteric fat and Retroperitoneal to weight of retroperitoneal fat.

After feeding the test diet for 10 weeks, the epididymal, perirenal, mesenteric, and retroperitoneal fat-pads contained in the visceral fat were removed and weighed. The cinchonine-supplemented group (CSID) showed significantly reduced weights of the epididymal (by 19%), perirenal (by 45%), mesenteric (by 43%), and retroperitoneal (by 15%) fat-pads as compared to the control group (HFD). The total visceral fat weight was significantly reduced by 26% in the CSID group than in the HFD group (p<0.001, FIG. 3). Accordingly, it would be appreciated that cinchonine has excellent effects to reduce body weights and visceral fat-pad weights.

Example 3

Prevention and Treatment of Hyperlipidemia, Fatty Liver and Type 2 Diabetes by Cinchonine Biochemical Analysis of Blood and Liver Tissues After 10 weeks of breeding, total cholesterol, triglyceride and glucose levels in the plasma and lipid levels in the liver tissue were measured as follows: Total cholesterol, triglyceride, free fatty acid and glucose levels in the plasma were measured twice for each using a commercially available kit (Bio Clinical System). The level of LDL+VLDL in plasma was calculated by subtracting HDL level from the total cholesterol level. The activities of ALT (alanine aminotransferase) and AST (aspartate aminotransferase) used as liver function indicator were measured using a commercially available kit (Bio Clinical System, Korea).

Lipids were extracted from the liver tissue according to Folch et al.'s method Folch J et al., *J Biol Chem*, 226: 497-509 (1957)). After adding 1 mL of distilled water to 0.25 g of the liver tissue, the liver tissue was homogenized using a Polytron homogenizer (IKA-Werke GmbH & Co., Ultra-Turrax, Staufen, Germany). After adding 5 mL of chloroform:methanol solution (2:1, v/v) to the homogenate and mixing well, the mixture was centrifuged at 1000×g for 10 minutes. After adding 2 mL of chloroform:methanol solution (2:1, v/v) again to the supernatant, the same procedure was repeated to completely separate the lipid components of the liver. After adding 3 mL of chloroform:methanol:0.05% $CaCl_2$ (3:48:47, v/v/v) solution to the remaining pellets and mixing well for 1 minute, followed by centrifugation at 1000×g for 10 minutes, the resulting pellets were completely dried with nitrogen gas. The dried lipids were dissolved in 1 mL of methanol and then analyzed. The commercially available kits (Bio Clinical System, Korea) were used to measure the levels of triglyceride, cholesterol and free fatty acids of the liver tissue.

Changes of Lipid Levels in Plasma and Liver Tissues

After feeding the test diet (Table 1) for 10 weeks, the cinchonine-supplemented group showed significantly lower plasma levels of triglyceride level (by 24%), total cholesterol level (by 30%), LDL+VLDL level (by 33%) and free fatty acid level (by 21%) as compared to the HFD group (Table 2). Moreover, cinchonine supplemented to the HFD resulted in a significant reduction of the fasting blood sugar level by 27%, as compared to HFD. The HFD group exhibited significantly higher plasma activities of ALT and AST, which are parameters for hepatic function, as compared to the normal diet group and the CSID group showed significantly decreased plasma activities of ALT (by 58%) and AST (by 46%) as compared to HFD group. Accordingly, it could be recognized that cinchonine has the excellent effects of improving hyperlipidemia, insulin resistance and hepatic function parameters in obesity induced by HFD.

After feeding the test diet for 10 weeks, absolute weight of liver (g) in the cinchonine-supplemented group (CSID) was significantly reduced by 36%, as compared to the HFD group and the ratio of the liver weight to the body weight (g/100 g body weight) in the cinchonine-supplemented group (CSID) was significantly reduced by 25%, as compared to the HFD group. The cinchonine-supplemented group showed significantly decreased levels of triglyceride (by 16%), cholesterol (by 16%) and free fatty acid (by 23%) in liver tissue as compared to HFD (Table 3). Accordingly, it would be understood that cinchonine significantly ameliorates fatty liver conditions in obesity caused by the high fat diet.

TABLE 2

|  | Normal diet group (ND) | High fat diet group (HFD) | Cinchonine-supplemented group (CSID) |
|---|---|---|---|
| Triglyceride (mmol/L) | $0.59 \pm 0.04^b$ | $0.90 \pm 0.01^a$ | $0.68 \pm 0.05^b$ |
| Total cholesterol (mmol/L) | $3.63 \pm 0.15^c$ | $6.57 \pm 0.13^a$ | $4.57 \pm 0.26^b$ |
| HDL cholesterol (mmol/L) | $1.34 \pm 0.12^a$ | $1.05 \pm 0.05^b$ | $0.89 \pm 0.04^b$ |
| LDL + VLDL cholesterol (mmol/L) | $2.29 \pm 0.12^c$ | $5.52 \pm 0.14^a$ | $3.68 \pm 0.27^b$ |
| Free fatty acid (uEq/L) | $572 \pm 42.8^c$ | $869 \pm 14.9^a$ | $685 \pm 65.6^b$ |
| Glucose (mmol/L) | $7.10 \pm 0.27^b$ | $8.97 \pm 0.63^a$ | $6.51 \pm 0.62^b$ |
| ALT (IU/L) | $9.42 \pm 0.96^b$ | $14.25 \pm 0.27^a$ | $5.94 \pm 0.78^c$ |
| AST (IU/L) | $7.38 \pm 0.66^b$ | $11.30 \pm 1.03^a$ | $6.03 \pm 0.28^b$ |

TABLE 3

|  | Normal diet group (ND) | High-fat diet group (HFD) | Cinchonine-supplemented diet group (CSID) |
|---|---|---|---|
| Liver weight (g) | $1.3 \pm 0.11^b$ | $2.2 \pm 0.22^a$ | $1.4 \pm 0.14^b$ |
| Liver weight (g/100 g body wt) | $3.5 \pm 0.21^b$ | $5.3 \pm 0.32^a$ | $4.0 \pm 0.12^b$ |
| Triglyceride (μmol/g) | $27.6 \pm 1.67^c$ | $70.9 \pm 3.71^a$ | $59.7 \pm 2.26^b$ |
| Cholesterol (μmol/g) | $33.9 \pm 0.83^c$ | $130.2 \pm 8.78^a$ | $109.9 \pm 2.37^b$ |
| Free fatty acid (μEq/g) | $16.1 \pm 0.89^c$ | $49.8 \pm 2.04^a$ | $38.6 \pm 3.52^b$ |

Example 4

Inhibition of Obesity-Related Gene Expressions in Mouse Visceral Fat Tissues by Cinchonine RNA Extraction by Trizol Method and Verification After adding 1 mL of Trizol agent (Invitrogen, USA) per 0.1 g of epididymal fat tissues, the mixture was homogenized and centrifuged at 12,000×g for 10 min at 4° C. The supernatant was transferred to a new tube and 200 μl of chloroform was added to the tube, followed by vortexing. The same procedure was repeated twice and then the supernatant was transferred to a new tube, followed by addition of isopropanol and the supernatant at 1:1 ratio. The mixture was vigorously shaken 10 times and then incubated for 10 min at room temperature, followed by centrifugation at 12,000×g for 10 min at 4° C. to remove the supernatant. After adding 1 mL of 70% ethanol to the remaining pellet, it was centrifuged at 7,500×g for 5 min at 4° C. After removing the ethanol, the RNA pellet contained in the tube was dried for 5 min at 4° C. and dissolved in nuclease-free water.

The RNA concentration of sample was measured at a wavelength of 260 nm and 280 nm using a UV/VIS spectrophotometer (Beckman coulter, DU730) and the integrity of RNA sample was verified by agarose gel electrophoresis.

RT-PCR (Reverse Transcription Polymerase Chain Reaction) Analysis

The RNA sample obtained from the epididymal fat tissues was transcribed using oligo dT primer and SuperScript reverse transcriptase (GIBCO BRL, Gaithersburg, Md., USA) to synthesize cDNA. The PCR amplification was performed using the cDNA as templates and primers complementary to cDNA 5' and 3' flanking sequence. The sequences of the primers used are presented in Table 4. The amplified products (1 μl) were resolved on 1% agarose gel electrophoresis.

TABLE 4

| Gene | Direction | Sequence (5'→ 3') | Annealing Temp (° C.) | Size of PCR product (bp) |
|---|---|---|---|---|
| PPARγ2 | F | TTCGGAATCAGCTCTGTGGA | 55 | 148 |
|  | R | CCATTGGGTCAGCTCTTGTG |  |  |
| aP2 | F | AGCATCATAACCCTAGATGG | 55 | 128 |
|  | R | GAAGTCACGCCTTTCATAAC |  |  |
| C/EBPα | F | TCGGTGCGTCTAAGATGAGG | 55 | 187 |
|  | R | TCAAGGCACATTTTTGCTCC |  |  |
| TNF-α | F | TGTCTCAGCCTCTTCTCATT | 55 | 156 |
|  | R | AGATGATCTGAGTGTGAGGG |  |  |
| IL-6 | F | ATGAAGTTCCTCTCTGCAAGAGACT | 55 | 638 |
|  | R | CACTAGGTTTGCCGAGTAGATCTC |  |  |
| UCP1 | F | GGGACCTACAATGCTTACAG | 55 | 103 |
|  | R | GGTCATATGTCACCAGCTCT |  |  |
| UCP3 | F | ACGGATGTGGTGAAGGTCCG | 55 | 464 |
|  | R | TACAAACATCATCACGTTCC |  |  |
| GAPDH | F | AGAACATCATCCCTGCATCC | 55 | 321 |
|  | R | TCCACCACCCTGTTGCTGTA |  |  |

RT-PCR Analysis Results of Epididymal Fat Tissues

Adipogenesis is a process in which preadipocytes are proliferated and differentiated to adipocytes, which is accompanied with changes of cell morphology and gene expression profiles. In adipogenesis, lipids are accumulated and adipocyte-specific genes such as aP2 (fatty acid binding protein), LPL (lipoprotein lipase) and adipsin are expressed under controls of three transcription factors including PPARγ (Peroxisome proliferator activated receptor gamma), C/EBPs (CCAAT enhancer-binding proterins) and SREBP-1c (sterol regulatory binding protein-1c).

Figure 4:
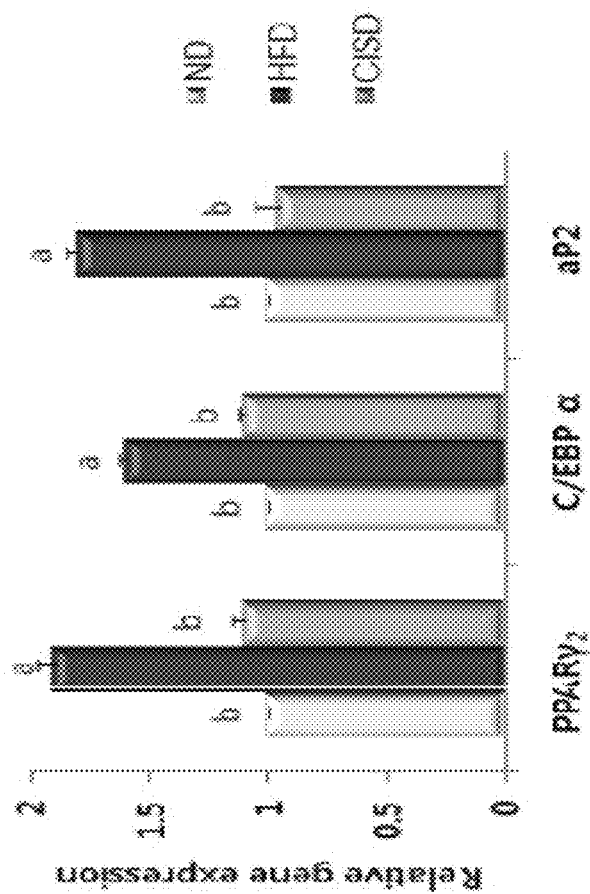
FIG. 4 represents the expression profiles of genes involved in adipogenesis in in mice visceral fat tissues. The left panel represents images of RT-PCR analysis results for PPARγ2, C/EBPα, and aP2, and the right panel represents relative expression levels of these genes. The data were normalized to GAPDH mRNA levels and expressed as relative values to those from ND mouse. The results are represented as mean±standard error of values obtained from eight mice. The characters above the bars indicate significant difference in dietary groups by one-way analysis of variance (ANOVA) test and Duncan's multiple range test (P<0.05).
Figure 4:
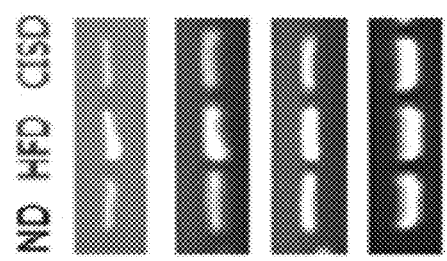

The mRNA expressions of epididymal fat tissues were evaluated by RT-PCR analysis. The HFD group showed significantly elevated expressions of C/EBPα, PPARγ2 and aP2 genes as compared to the ND group. Nuclear transcription factors, C/EBPα and PPARγ2 play an important role in adipogenesis and aP2 is a target gene for these transcription factors. In contrast, the cinchonine-fed group (CSID) showed significantly reduced expressions of C/EBPα, PPARγ2 and aP2 genes to similar levels to the ND group (FIG. 4). Accordingly, it would be understood that cinchonine contributes to decreased expressions of nuclear transcription factors and their target gene playing a critical role in adipogenesis in visceral fat tissues, thereby suppressing the amount of visceral fats.

It was well known to one of skill in the art that diet-induced obesity animal models or obese humans exhibit Type 2 diabetes showing simultaneously elevated blood insulin and glucose levels in fasted state. A term "metaflammation" was recently coined to indicate inflammations induced by excess supply of nutrients or metabolites and obesity was indicated as chronic and low-level inflammation, highlighting the correlation between obesity and immune system. For example, the TLR4 (toll-like receptor 4) molecule responsible for innate immune responses plays a pivotal role in inflammation and insulin resistance pathway in response to dietary fats (particularly, saturated fatty acids) as ligands. When obesity is induced by HFD, the free fatty acids (especially saturated fatty acids) in body fluids are increased. The free fatty acids as ligands bound to TLR4 activate IKK and then NF-κB, and stimulate the secretion of pro-inflammatory cytokines such as TNF-α and IL-6 to cause inflammatory response. In addition, TNF-α and IL-6 activate both the cytokine signaling 3 (SOCS3) and JNK and induce phosphorylation of serine residues of insulin receptor substrates (IRS) to inhibit glucose transport, finally causing insulin resistance in peripheral tissues of liver or muscle.

Figure 5:
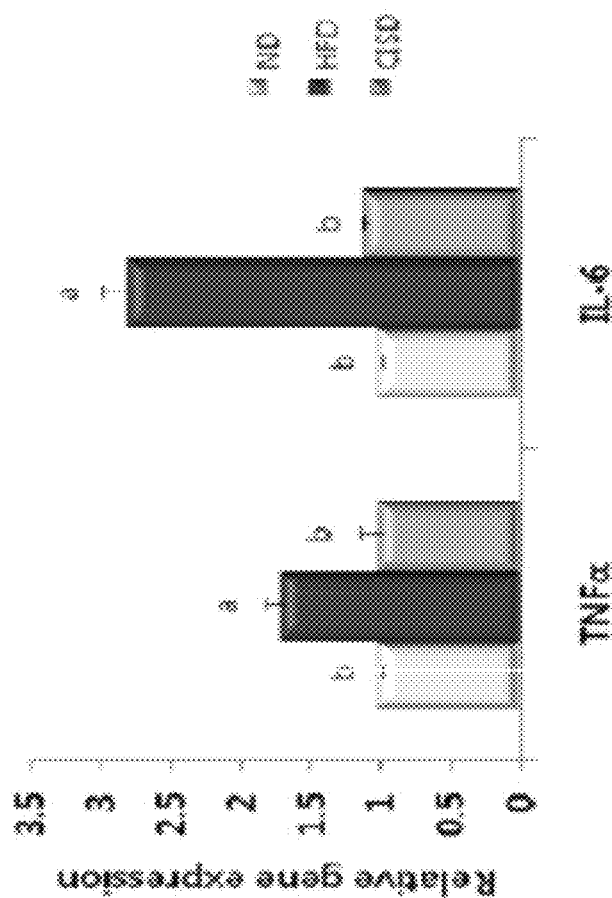
FIG. 5 represents change of gene expression profiles of pro-inflammatory cytokines in mice visceral fat tissues. The left panel is gel images of RT-PCR for TNF-α and IL-6, and the right panel represents relative expression levels of the genes. The data were normalized to GAPDH mRNA levels and expressed as relative values to those from ND mouse. The results are represented as mean±standard error of values obtained from eight mice. The characters above the bars indicate significant difference in dietary groups by one-way analysis of variance (ANOVA) test and Duncan's multiple range test (P<0.05).
Figure 5:
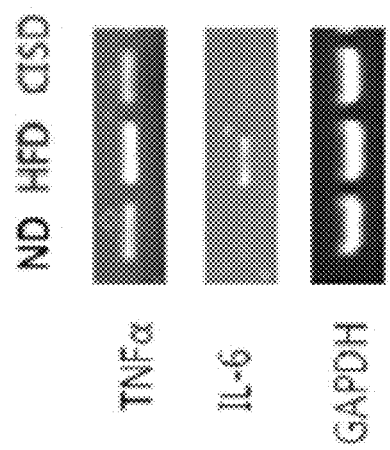

The mRNA expression profiles of pro-inflammatory cytokines in visceral fat tissues were evaluated using RT-PCR. The HFD group exhibited significantly higher levels of both TNF-α and IL-6 gene expressions as compared to the ND group. Meanwhile, these HFD-induced elevations in expressions of TNF-α and IL-6 were significantly reversed by feeding cinchonine (FIG. 5). Accordingly, it would be concluded that cinchonine has the excellent effects of decreasing chronic inflammation caused by obesity in the visceral fat tissues.

The dysfunction of mitochondria is related to senescence, heart diseases and gastrointestinal, endocrine and neurological disorders. The damages of the oxidation process in mitochondria increase glucose production in liver tissues and hyperglycemia, finally causing fatty liver. The mitochondria forms proton gradient across its inner and outer membranes by the electron transport chain, and generates ATP through $F_0F_1$-ATPase using the proton gradient as a driving force. Where $F_0F_1$-ATPase is not normally worked, the proton gradient disappears through uncoupling proteins to generate heat. In current, it has been reported that UCPs in adipose tissues promotes thermogenesis with maintaining redox balance by the energy-dissipatory mechanism. Therefore, UCPs as well as AMPK (AMP-activated protein kinase) become highlighted as novel targets for obesity treatment.

Figure 6:
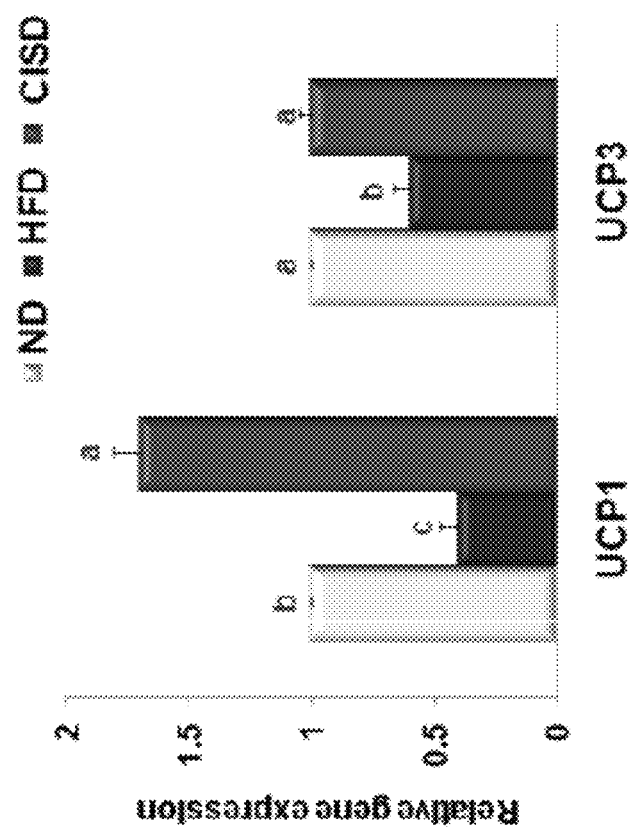
FIG. 6 represents change of gene expression profiles of UCPs in mice visceral fat tissues. The left panel is gel images of RT-PCR for UCP1 and UCP3, and the right panel represents relative expression levels of the genes. The data were normalized to GAPDH mRNA levels and expressed as relative values to those from ND mouse. The results are represented as mean±standard error of values obtained from eight mice. The characters above the bars indicate significant difference in dietary groups by one-way analysis of variance (ANOVA) test and Duncan's multiple range test (P<0.05).
Figure 6:
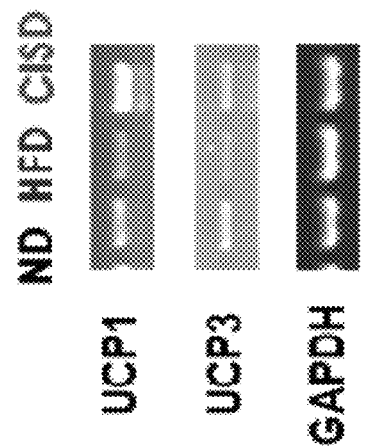

The expressions of UCP1 and UCP3 regulating thermogenesis in body were analyzed by RT-PCR using mRNA extracted from visceral fat tissues of rats fed with the test diet. The expressions of UCP1 and UCP3 genes were significantly decreased in the HFD group compared with the ND group. Meanwhile, these HFD-induced decrease in expressions of UCP1 and UCP3 were significantly reversed by feeding cinchonine to the similar level to the ND group (FIG. 6). Therefore, it would be understood that cinchonine significantly improves obesity-caused inhibition of thermogenesis in visceral fat tissues.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for decreasing lipid levels, treating obesity, or treating fatty liver in a subject in need thereof, the method comprising administering to the subject a composition comprising cinchonine as an active ingredient.

2. The method according to claim 1, wherein the composition reduces differentiation of adipocytes.

3. The method according to claim 1, wherein the composition decreases blood fat, liver fat or visceral fat.

4. The method according to claim 3, wherein the fat comprises triglyceride, cholesterol or free fatty acids.

5. The method according to claim 3, wherein the visceral fat is one or more selected from the group consisting of epididymal fat, perirenal fat, mesenteric fat and retroperitoneal fat.

6. The method according to claim 1, wherein the composition decreases the level of ALT (alanine aminotransferase) or AST (aspartate aminotransferase).

7. The method according to claim 1, wherein the composition decreases the expression of PPARγ (Peroxisome proliferator activated receptor gamma), C/EBPs (CCAAT enhancer-binding proteins) or aP2 (fatty acid binding protein).

8. The method according to claim 1, wherein the composition decreases the expression of TNF-α (tumor necrosis factor-alpha) and IL-6 (interleukin-6).

9. The method according to claim 1, wherein the composition increases the expression of UCP2 (uncoupling protein 2) or UCP3 (uncoupling protein 3).

10. The method according to claim 1, wherein the composition decreases the glucose level in blood.

11. The method according to claim 1, wherein cinchonine is derived from plants.

12. The method according to claim 1, wherein the composition is a pharmaceutical composition.

13. The method according to claim 1, wherein the composition is a food composition.

* * * * *